United States Patent [19]

Pekkarinen et al.

[11] 4,346,705
[45] Aug. 31, 1982

[54] METERING APPARATUS HAVING RATE COMPENSATION CIRCUIT

[75] Inventors: Michael O. Pekkarinen, Lincolnshire; Norm Shim, Glenview, both of Ill.

[73] Assignee: Baxter Travenol Laboratories, Inc., Del.

[21] Appl. No.: 195,432

[22] Filed: Oct. 9, 1980

[51] Int. Cl.³ .......................................... A61M 31/31
[52] U.S. Cl. .................................. 128/214 F; 73/4 R; 235/92 FL
[58] Field of Search ........... 128/214 C, 214 E, 214 F, 128/DIG. 12, DIG. 13, DIG. 218 A; 73/4, 861.03; 235/92 TF, 92 FQ, 92 FL, 92 CT

[56] References Cited

U.S. PATENT DOCUMENTS

| | | | |
|---|---|---|---|
| 3,895,529 | 7/1975 | Moore | 73/861.03 |
| 4,037,598 | 7/1977 | Georgi | 128/DIG. 12 X |
| 4,048,474 | 9/1977 | Olesen | 128/214 E X |
| 4,094,318 | 6/1978 | Burke et al. | 128/DIG. 13 X |
| 4,205,238 | 5/1980 | Shim et al. | 235/92 FL X |
| 4,210,138 | 7/1980 | Jess et al. | 128/DIG. 13 X |

Primary Examiner—Kyle L. Howell
Assistant Examiner—Francis J. Jaworski
Attorney, Agent, or Firm—P. C. Flattery; John P. Kibby, Jr.; Eugene Cummings

[57] ABSTRACT

A system for infusing fluids into the human body includes a peristaltic-type metering apparatus which controls the flow of fluid through a disposable administration set at a preset rate. A compensating circuit within the metering apparatus automatically varies the operating rate of the metering apparatus to compensate for dimensional variations in the apparatus and the tubing.

14 Claims, 11 Drawing Figures

METERING APPARATUS HAVING RATE COMPENSATION CIRCUIT

BACKGROUND OF THE INVENTION

The present invention relates generally to fluid infusion systems, and more particularly to an improved flow metering apparatus for such systems.

The infusion of fluids into the human body is usually accomplished by means of an administration set in conjunction with metering apparatus which controls the rate of fluid flow through the set. Peristaltic-type metering apparatus, which function by repetitively compressing and expanding a section of tubing, have proven particularly attractive since they do not introduce the possibility of leakage or contamination into the system, while providing positive control of fluid flow through the system.

One form of peristaltic-type metering apparatus which is particularly well adapted for infusion applications is described in U.S. Pat. No. 4,155,362, issued to Thurman S. Jess on May 22, 1979, and assigned to the present assignee. Basically, this apparatus includes individually spring-biased rollers mounted on a stepper motor-driven rotor which compress tubing of an administration set against a stationary platen, and a spring-biased plunger which restricts the lumen of the tubing downline of the rotor to provide a back pressure against which the rollers must work. This back pressure prevents the release of dissolved gas in the tubing, assists in restoring the tubing to its original shape following compression by the rollers, and prevents uncontrolled gravity flow in the event of failure of the apparatus.

In many applications, such as where medication is being administered, it is necessary that the operation of the metering apparatus be very precisely controlled to infuse only a preset volume of fluid at a preset rate. Unfortunately, manufacturing tolerances encountered in the apparatus and tubing, particularly in the metering head, may introduce metering errors unique to individual units which must be individually compensated for. In some cases this has required the fabrication and installation of unique gearing between the stepper motor and the rotor, which undesirably added to the cost of the apparatus. The metering apparatus of the present invention incorporates a novel rate compensating circuit which automatically varies the rotation rate of the rotor to compensate for rate errors, thereby obviating the need for unique gearing for individual units.

Accordingly, it is a general object of the present invention to provide a new and improved system for infusing fluids into the human body.

It is a more specific object of the present invention to provide a new and improved metering apparatus for use in conjunction with an administration set for infusing fluids into the human body.

It is another object of the present invention to provide a peristaltic-type pump and control system which provides for accurate administration of a predetermined quantity of fluid at a predetermined rate.

It is another object of the present invention to provide a fluid metering apparatus which provides improved metering accuracy.

It is another object of the invention to provide a self-contained fluid metering apparatus which is simple and convenient to use.

SUMMARY OF THE INVENTION

The invention is directed to metering apparatus for maintaining the flow of fluid through a fluid infusion set at a predetermined preset rate. The metering apparatus includes a housing, a rotor mounted on the housing for rotation about a fixed axis and having a plurality of circumferentially-disposed pressure rollers, and a pressure plate for positioning a tubing segment of the administration set in compressive engagement with the rollers whereby fluid is pumped through the tubing segment with rotation of the rotor. Means including a stepper motor are provided for driving the rotor. The stepper motor is driven by a source of repetitive clock pulses through a pulse divider circuit providing a user-entered first multiplication factor, and a rate compensating circuit providing a preset second multiplication factor, the divider and compensating circuits together providing a stepping signal to said stepper motor upon each occurrence of a predetermined number of the clock pulses whereby said rotor is caused to meter fluid through the tubing at the predetermined rate.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
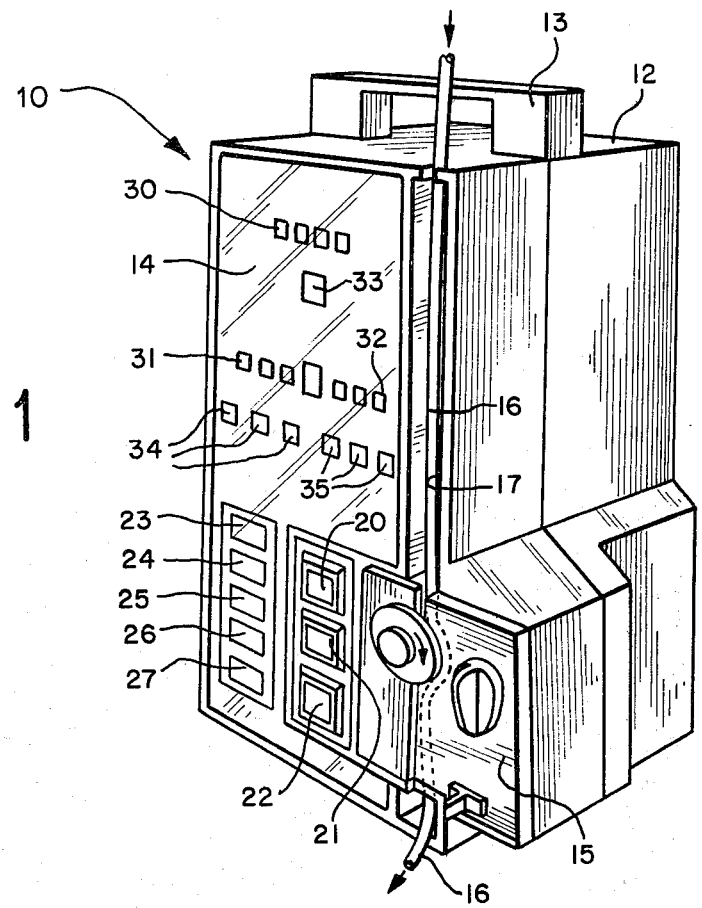
FIG. 1 is a perspective view of an infusion metering apparatus constructed in accordance with the invention.

Referring to the Figures, and particularly to FIG. 1, a peristaltic-type flow metering system 10 for use in conjunction with an administration set for controlling the flow of fluid into a vein or artery includes a generally rectangular housing 12 having a handle 13 at one end thereof for convenient carrying. The front surface of the housing includes a control panel 14 which allows the operator to control and monitor the operation of the metering apparatus, and a peristaltic-type flow metering head 15 for compressing a section of tubing 16 of the administration set to effect control of fluid flow therein. A channel 17 is provided above the metering head 15 for maintaining a portion of the tubing segment in a convenient view of the operator whereby flow irregularities can be more readily observed.

The administration set, of which tubing segment 16 is a part, and which may be conventional in design and construction, is preferably formed of a plastic material such as vinyl and packaged in a sterile and non-pyrogenic condition. To avoid the danger of contamination, the administration set is normally utilized for one application only, and is disposed of after use.

The operating mode of the metering apparatus is controlled by means of a push button STOP switch 20, a push button START switch 21, and a push button power ON-OFF switch 22. Each of these push button switches includes an internal indicator lamp which provides a positive indication of the operating mode of the apparatus.

Various abnormal operating conditions are annunciated by means of indicator lights 23-27 contained on the control panel to the left (as viewed in FIG. 1) of the mode control push buttons. The operation of these indicator lights will be explained in conjunction with the operation of their respective systems within the metering apparatus.

Control panel 14 further includes a digital display 30 of volume infused, a digital display 31 of volume to be infused, and a digital display 32 of the fluid flow rate. The volume displayed by display 30 is the volume of fluid actually infused, and can be reset to 0 by the operator by means of a push button RESET switch 33. The volume to be infused by display 31 is preset by the operator by means of a set of push button switches 34 to indicate a desired volume of fluid to be infused. Similarly, the infusion rate display 32 is preset by the operator by means of a second set of push button switches 35 to indicate the rate at which infusion is to take place.

Figure 2:
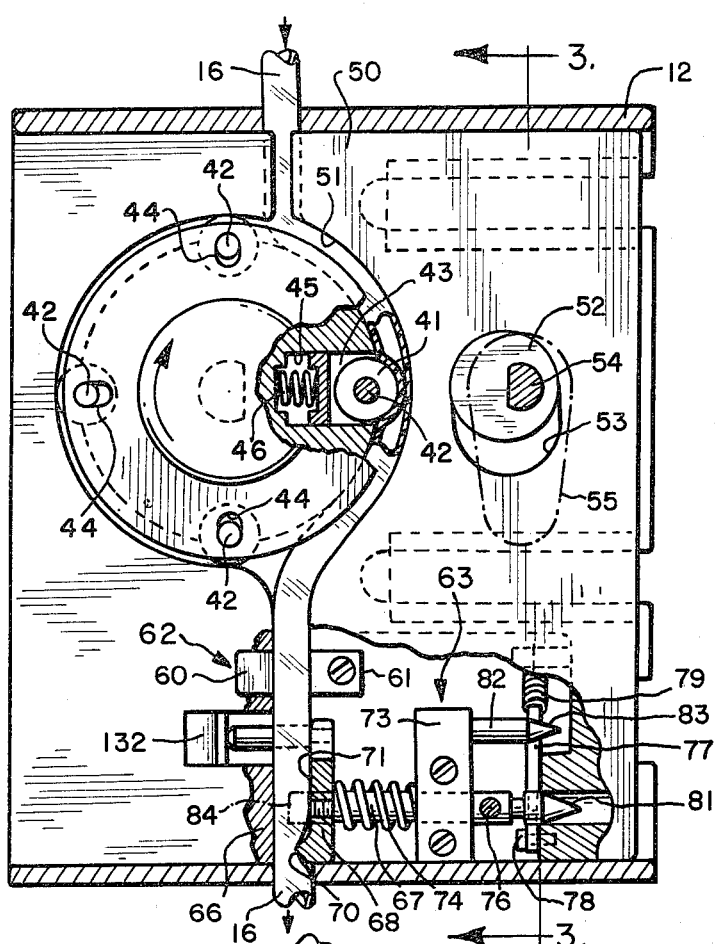
FIG. 2 is an enlarged front elevational view of the peristaltic pump utilized in the metering apparatus of FIG. 1 broken away to show the rotor and downline occlusion stations thereof.

Referring to FIG. 2, the peristaltic metering head 15 includes a rotor assembly 40 having four pressure rollers 41 disposed in equi-spaced relation about its circumference. The rollers are mounted on respective shafts 42 for free rotation, and the shafts are carried on respective carriage assemblies 43 constrained to radial movement by respective radial slots 44 and radially aligned recesses 45. The rollers are spring loaded in radially outward directions by respective helical springs 46 disposed within the recesses.

The pump also includes a pressure plate 50 having an arcuate working surface 51 which substantially corresponds in shape to the circumference of the pump rotor and is positioned to bring the tubing segment 16 into compressive engagement with rollers 41 around at least a portion of the rotor circumference extending between adjacent rollers. The pressure plate may be reciprocated toward and away from rotor 40 to facilitate installation and removal of tubing segment 16 by rotation of an eccentric cam 52, which is constrained to operate within a vertical slot 53 provided on the pressure plate. Rotation of the cam is accomplished by a shaft 54 and user-actuable level 55 operatively connected to the cam. When the lever 55 is in its bottom position, as shown in FIG. 2, the pressure plate is moved sufficiently close to the rotor circumference to cause tubing segment 16 to be completely occluded by the rollers. Since each of rollers 41 is individually biased into engagement with the tubing segment, the pressure applied by each roller is independent of the number of rollers engaging the tubing segment.

After passing through the peristaltic metering station, tubing segment 16 extends between a light source 60 and a photodetector 61, which together comprise a bubble detector station 62. As will be seen presently, it is the function of this station to discontinue operation and alert the operator upon formation of a bubble in the tubing segment.

Figure 3:
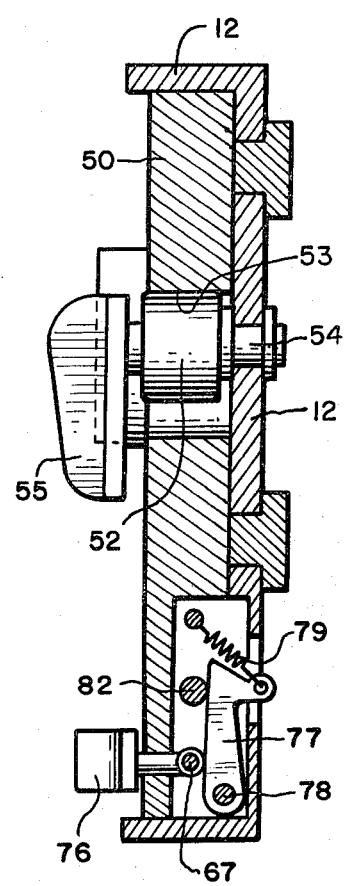
FIG. 3 is a cross-sectional view of the pump taken along line 3—3 of FIG. 2.
Figure 3A:
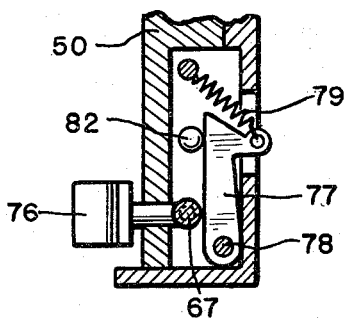
FIGS. 3a and 3b show the latch member of the downline occlusion station as shown in FIG. 3 in alternate open and closed positions.

Referring to FIGS. 2-3, the tubing next passes through a flow restriction station 63. This station includes a pressure block 66 and a slidably mounted flow restriction plunger 67 biased against the sidewall of tubing segment 16. The end of plunger 67 which engages the tubing segment includes a generally L-shaped head portion 68 having a wedge-shaped working surface 70 and a generally flat control surface 71. Plunger 67 includes a central body portion which is slidably received within a stationary mounting block 73, and which extends through the center of a helical compression spring 74 provided for biasing head 68 into engagement with tubing segment 16.

The working surface 70 of head portion 68 bears against the sidewall of tubing segment 16 substantially perpendicular to the direction of fluid flow within the tubing as the tubing is held in position against pressure block 66. As a result, the lumen of the tubing segment is occluded at the point of engagement, and a downline conduit segment is defined between the point of engagement of the rollers 41 and the point of engagement of the wedge-shaped working surface 70. As previously developed, the occlusion of the tubing in this way increases the pressure of the fluid in the tubing segment and prevents separation of dissolved gases therein.

The control surface 71 of plunger 67 extends substantially parallel to the direction of fluid flow and is substantially greater an area than the working surface 70. The relatively large area of the control surface 71 renders the plunger more sensitive to pressures in the tubing lumen when the pump is operative so that higher pressures can be exerted by spring 74 to more positively close off the tubing when the pump is not in operation, without detriment to its ability to open at lower operating pressures.

Plunger 67 may be opened to facilitate loading or unloading of tubing segment 16 by means of a user-actuated lever 76 mounted for reciprocation with plunger 67. The plunger is constrained to reciprocation along a defined operating path by the stationary mounting block 73 which is mounted to the apparatus housing 14. The helical compression spring bears against this mounting block at one end and against the head of the plunger at its other end, causing the desired bias of the plunger against the tubing segment.

Figure 2A:
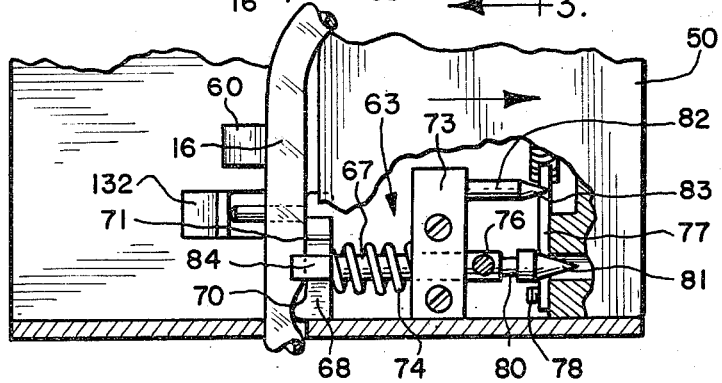
FIGS. 2a and 2b show the downline occlusion station of the pump as seen in FIG. 3 in alternate open and closed positions.
Figure 2B:
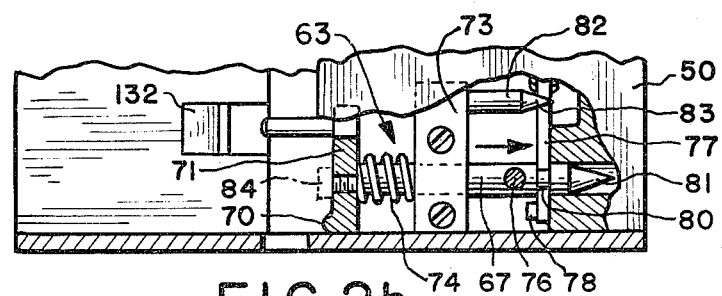
Figure 3B:
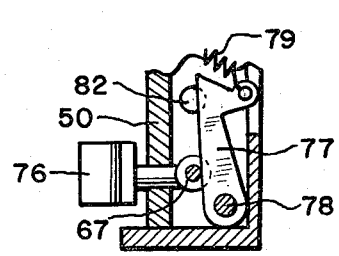

Automatic release of the plunger is obtained by means of a latch member 77 which is pivotably mounted at 78 to pressure plate 50 and biased by a helical spring 79 for operation within a plane perpendicular to the plunger. The plunger includes a slot 80 in which the latch member 77 is received when the plunger is moved to its full open position, as shown in FIG. 2b. The end 81 of the plunger may be tapered to facilitate displacement of the latch member prior to seating in slot 80. Once the latch member has been received in the slot, the plunger is locked open and the tubing segment 16 can be readily removed.

Figure 4:
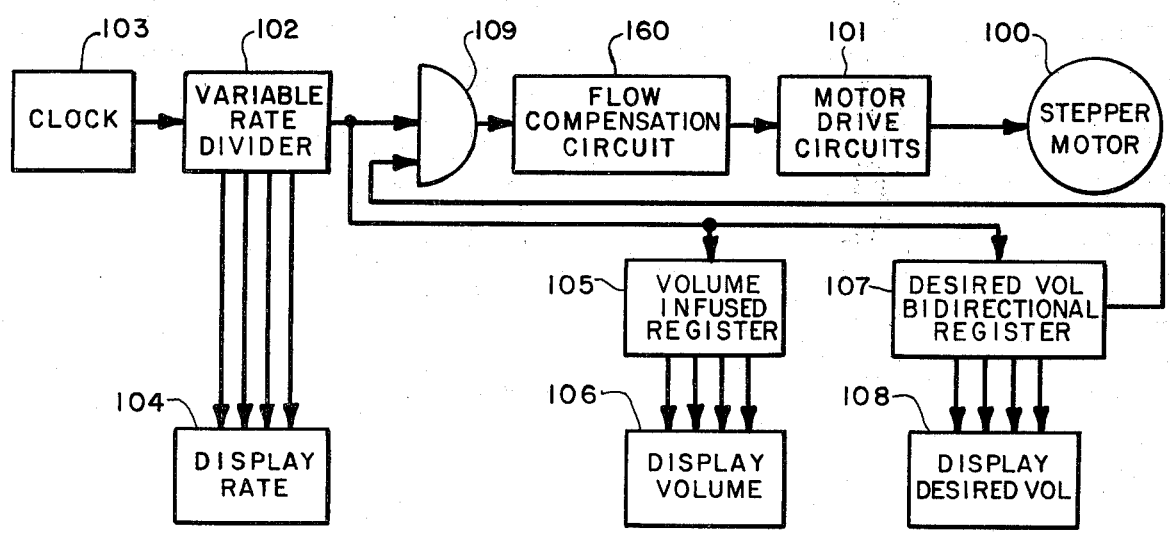
FIG. 4 is a simplified functional block diagram of the control system incorporated in the metering apparatus of the invention.

To insure that plunger 67 will be released when pressure plate 50 is subsequently closed, mounting block 73 is provided with an actuator pin 82. As shown in FIGS. 3 and 4, this actuator pin has a tapered end surface 83 which serves to displace the pivotably mounted latch member 77 from slot 80 when the pressure plate is returned to its closed position by rotation of knob 55. In this way, the plunger is automatically released so as to again become spring-biased against the administration set tubing segment 16 as the metering station is closed. This prevents inadvertent operation of the system without the back pressure and gravity flow protection provided by the plunger. Also, when the pressure plate is closed, the displacement of latching member 77 prevents the plunger from being latched open. A gate member 84 adjacent the control surface 71 of plunger 67 prevents the tubing segment from being inadvertently pulled free of the compression plunger during operation.

By reason of the tubing segment 16 being held in a highly visible vertical position within channel 17 the flow of fluid therethrough can be readily monitored. Furthermore, this channel obviates the need for additional tubing clamps at the inlet and outlet portions of metering head 15 while at the same time providing an aesthetically pleasing structure on the pump housing.

Referring now to FIG. 4, the control system for metering apparatus 12 is seen to include a stepper motor 100 which is rotatably coupled to rotor 40 so as to drive the rotor one increment for each step command applied to the motor. To supply the multi-phase signals required for operation of the stepper motor the metering apparatus includes multi-phase motor drive circuits 101 which respond to a control pulse applied through a rate compensation circuit 160 to generate a multi-phase output signal which steps the motor one increment. The control pulses are generated by a variable rate divider 102 which produces an output signal after a predetermined number of input pulses have been received from a continuously running clock 103. The divider, which may be conventional in design and construction, is preset by the user to a desired division rate which is displayed by an associated display device 104. In this way, by setting different division factors into the variable rate divider 102, the stepper motor can be operated over a wide range of rotational speeds.

To provide a display indicative of the total volume of fluid infused a register 105 responsive to the output pulses from divider 102 is provided. The counting state of register 105, and hence the volume infused, is displayed by a display device 106. The output pulses from divider 102 are also applied to a register 107 having an associated display device 108. This register is a bi-directional register, which prior to use of the metering apparatus is counted up to a counting state corresponding to the quantity of fluid to be infused, and then during use is counted down with infusion of the fluid until a zero counting state is reached. At this time the register generates an output signal which disables a gate 109 to interrupt application of control pulses to motor drive circuits 101.

Figure 5:
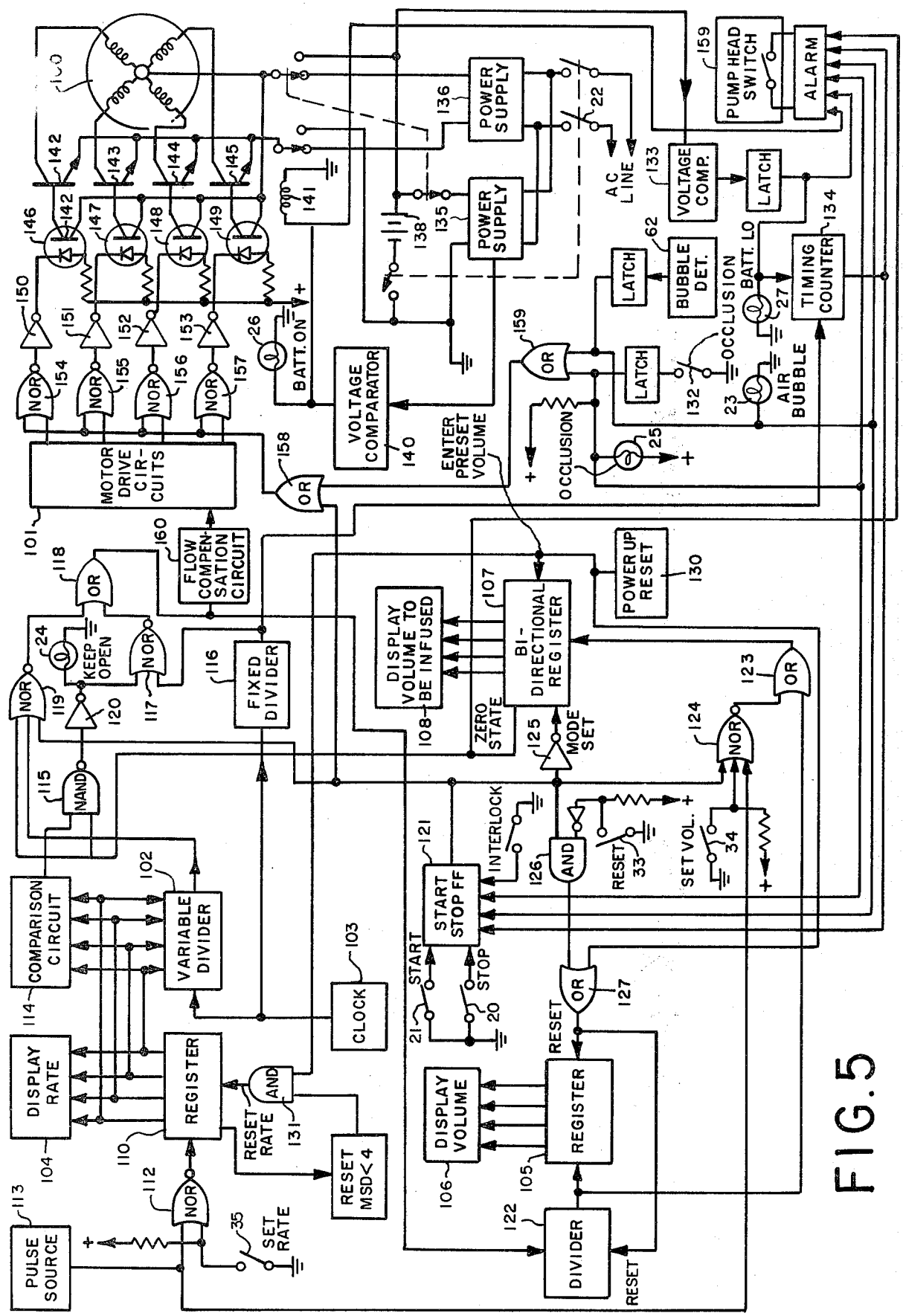
FIG. 5 is a functional block diagram partially in schematic form of the control system.

The control system of the flow metering apparatus 10 is shown in greater detail in FIG. 5. Here the division factor of variable divider 102, and hence the fluid infusion rate, is seen to depend on the counting state of a register 110. This counting state can be conveniently set by the user by means of the rate setting switches 35 which enable respective NOR gates 112 to supply pulses to the register from a pulse source 113. In practice, multiple NOR gates and rate setting switches are provided to allow each digit of the register to be independently set. The counting state of register 110 is displayed by display device 104 as an indication of the metering or infusion rate of the apparatus.

The output of register 110 is applied to a comparison circuit 114 wherein the register counting state is compared with a predetermined fixed minimum rate, typically 5 ml. per hour, to determine whether the infusion rate established by divider 102 is greater than or less than the minimum rate. In the event that the desired rate is greater than the minimum rate, comparison circuit 114 produces an output signal which enables NAND gate 115 to provide for establishment of a minimum "keep open" rate after the desired quantity of fluid has been infused. To this end, the output of clock 103 is applied to a fixed divider 116 which provides output pulses at a fixed minimum "keep open" rate. These pulses are applied to a NOR gate 117 and, depending on the state of this gate, to an OR gate 118 for application through rate compensation circuit 160 to the motor drive circuits 101. The "keep open" mode is operative only after the desired quantity of fluid has been infused, as signaled by the bi-directional register 107 reaching a zero counting state.

The output signal generated by register 107 upon reaching a zero counting state is applied to the remaining input of NAND gate 115 and to one input of a NOR gate 119. As a result, NOR gate 119 is inhibited and the application of pulses from variable divider 102 is interrupted. Should NAND gate 115 be enabled as a result of the variable rate being greater than the predetermined minimum flow rate, the zero state output signal from register 107 is applied through an inverter 120 to a keep open indicator 24 and to an input of NOR gate 117, wherein it serves as an enabling signal. This gate, when enabled, allows the fixed rate pulses from the fixed rate divider 116 to be applied to OR gate 118, and hence through rate compensation circuit 160 to motor drive circuits 101. In this way, a minimum flow rate is maintained even after the desired quantity has been infused.

To provide start-stop control over stepper motor 100 the remaining inputs of NOR gates 117 and 119 are connected to the output of a start-stop flip-flop 121. This flip-flop may be conditioned to a start state by actuation of the push button START switch 21, or to a stop state by actuation of the push button STOP switch 20, or by occurrence of any one of a number of abnormal conditions, including interruption of power, detection of a bubble in the administration set, detection of an occlusion in the administration set, or the opening of the metering head pressure plate while the metering apparatus is in operation.

To provide an accurate indication of the volume of fluid actually infused, the output of OR gate 118 is applied to a fixed divider stage 122 wherein a constant division factor is applied to generate one output pulse for each milliliter of fluid infused. Assuming that stepper motor 100 is required to step 2,353 times to pump 1 milliliter through tubing segment 16, and rate compensation circuit 160 has a nominal correction factor of N where no correction is required, then divider 122 may be set to divide by 2,353×N to obtain the desired volume-indicative output signal. This output signal is applied to register 105 wherein it advances the counting state of the register so that the instantaneous counting state thereof indicates the volume of fluid actually infused. As previously stated, this volume is displayed by display device 106.

The volume-indicative output pulses from divider 112 are also applied through an OR gate 123 to the stepping input of bi-directional register 107 wherein they cause that register to count down one step toward zero with each milliliter passing through the system. As stated previously, the counting state of register 107, and hence the volume of fluid to be infused, is displayed by display device 108.

Prior to use of the infusion metering apparatus, the counting state of register 107 is preset by the user by momentarily applying pulses to the register from pulse source 113. This is accomplished through a NOR gate 124 which is enabled by the operator by actuation of the SET VOLUME switch 34. In practice, one such switch and NOR gate are provided for each decade of the counter. The remaining input of NOR gate 124 is connected to the output of the start-stop flip-flop 121 to prevent the volume display from being changed while the metering apparatus is in operation.

Register 107 is capable of counting either up or down depending on an applied mode control signal. This signal is developed from the output of start-stop flip-flop 121 by means of an inverter 125 so as to condition register 107 to count up with application of set pulses from source 113 when the apparatus is stopped, and to count down with application of volume-indicative pulses from divider 122 when the metering apparatus is in operation.

Prior to initial operation of the metering apparatus register 105 is reset by the operator by actuation of push button RESET switch 33. This switch is connected to one input of an AND gate 126, the other input of which is connected to the output of the start-stop flip-flop 121 to render the reset switch 33 non-functional while the metering apparatus is in operation. The output of AND gate 126 is applied through an OR gate 127 to the reset inputs of register 106 and divider 122. In this way, the divider and register are simultaneously reset to a zero counting state prior to initial operation of the apparatus.

An auto reset state 130 responsive to initial application of power to the apparatus is provided to automatically establish an initial counting state in registers 105, 107 and 110. The output of the auto reset stage is applied to the remaining input of OR gate 127 so as to establish a zero counting state in register 105 and divider 122, and to the reset input of register 110 through AND gate 131. Should the operator attempt to set the most significant digit of register 110 above 4, a reset circuit coupled to the remaining input of AND gate 131 also resets the register. In this way the setting of infusion rates in excess of 455 ml. per hour is prevented. The output of the auto reset stage is also applied to register 107, wherein it establishes a minimum counting state of 1 ml. to prevent initiation of the "keep open" mode before the metering apparatus has been placed in operation.

Operation of the infusion metering apparatus is interrupted upon occurrence of an occlusion within the administration set, as detected by a switch 132 associated with plunger 67 (FIGS. 3 and 5). This switch, which may be a pressure switch similar to switches 33–35, or a magnetically-actuated Hall-effect switch, is actuated by an actuator lever attached to the plunger when the plunger is allowed to close against the tubing as a result of an occlusion within the administration set. The switch provides an output signal which actuates a latch circuit to condition start-stop flip-flop 121 to a STOP state and illuminates occlusion indicator lamp 25.

Operation of the apparatus is also interrupted in the event of a bubble being detected at bubble detector 62. In this event, an output signal is generated by the bubble detector which actuates a latch circuit to condition the start-stop flip-flop 121 to interrupt operation of the metering apparatus. At the same time, BUBBLE indicator lamp 23 is illuminated to alert the operator.

Operating power for the fluid metering apparatus is supplied by means of two unidirectional current supplies 135 and 136 which receive operating power from the AC line through ON-OFF switch 22. A battery 138 is provided as an additional source of operating power in the event of failure of the AC line. The battery is connected through switch 22 across the output of power supply 135.

Normally, battery 138 is maintained charged by power supply 135 and the various control circuits of the infusion metering apparatus are powered by this combined source, while the stepper motor 100 is powered by the power supply 136. To guard against interruption of AC line voltage the output of the power supply 135 is continuously monitored by a voltage comparator 140. Upon occurrence of a line voltage interruption an output signal is produced by comparator 140 which simultaneously illuminates a BATTERY ON indicator 26 and actuates a relay 141.

Operation of the metering apparatus is interrupted whenever the battery voltage falls below a predetermined minimum level for a predetermined period of time. To this end, the battery voltage is continuously monitored by a voltage comparator stage 133. Upon occurrence of a low voltage condition, an output signal is produced which activates a latch circuit to illuminate the BATTERY LOW lamp 27 and initiate operation of a timing counter 134. This counter counts the "keep open" output pulses developed by fixed divider 116 to obtain a 10 minute time delay. If the low voltage condition persists beyond this delay period an output signal is developed by timing counter 134 which causes the BATTERY LOW lamp to flash and conditions start-stop flip-flop 121 to interrupt operation of the metering apparatus. It should be noted that the operation of comparator 133 is entirely independent of comparator 140, and serves as a check on system voltage whether supplied by power supply 135 or battery 138.

Stepper motor 100 is powered by power supply 136 through transfer contacts on relay 141. The purpose of these contacts is to substitute battery 138 as a source of power for the stepper motor in the event of an AC line failure as detected by comparator 140. The various phase windings of motor 100 are individually supplied from power supply 136 by means of switching transistors 142–145 connected in series with the windings.

Isolation is obtained between stepper motor 100 and the pulse-sensitive control circuits of the metering apparatus by means of individual optical isolators 146–149 associated with respective ones of the switching transistors. Each of the optical isolators includes a light detecting element connected between the motor current source and a respective one of the switching transistors, and a light emitting diode (LED) element connected to the output of a respective one of inverting amplifiers 150–153. These amplifiers receive phase control signals from motor drive circuits 101 through respective NOR gates 154–157 which serve as a safety shutoff control means for the metering apparatus.

The NOR gates 154-157 are disabled when the start-stop flip-flop 121 is conditioned to a stop mode by means of an OR gate 158 having an output connected to one input of each of the NOR gates. Also, these NOR gates can be disabled by outputs from bubble detector 62 and occlusion switch 132 through an additional OR gate 159 which provides an additional input to OR gate 158. Thus, occurrence of an occlusion, detection of a bubble, or conditioning of the start-stop flip-flop to a stop state for any reason causes the interruption of control signals to optical isolators 146-149 and interruption of drive power to stepper motor 100.

In operation, the user initially sets an infusion rate by actuating switch 35 to apply a requisite number of pulses to register 110. The counting state of this register sets the variable divider 102 such that control pulses are developed at the output thereof with a repetition rate commensurate with the desired infusion rate. These control pulses are applied through NOR gate 119 and rate compensation circuit 120 to the motor drive circuits 101 wherein they are utilized to generate multiple phase control signals suitable for controlling the operation of the multiphase stepper motor 100. Each of the phase signals developed by drive circuits 101 is applied through a respective one of NOR gates 154-157 and inverter amplifiers 150-153 to a respective one of optical isolators 146-149. These isolators in turn control conduction in respective ones of drive transistors 142-145 to apply current from power supply 136 to stepper motor 100. In this way, the stepper motor turns the peristaltic rotor 40 at a rate established by the operator.

To provide a continuous readout of fluid volume infused the drive pulses applied to rate compensation circuit 160 are also applied to divider 122 to develop pulses indicative of the number of complete milliliters infused. These pulses are counted by register 105 to provide a display in device 106 indicative of the actual quantity of fluid infused.

Prior to initial operation of the apparatus an initial counting stage is established in register 107 by momentary application of pulses from pulse source 113 through NOR gate 124 and OR gate 123 to establish an initial counting state indicative of the total volume of fluid to be infused. Register 108 is conditioned to count up at this time by start-stop flip-flop 121 through inverter 125.

Once this volume is set, operation is started by actuation of switch 21 and register 107 is conditioned to count down by flip-flop 121. Pulses from divider 122 indicative of actual volume infused are now applied through OR gate 123 to count register 107 down toward zero. When the register reaches a zero counting state, indicating that the desired volume of fluid has been infused, an output signal from register 107 inhibits NOR gate 119 and prevents further operation of stepping motor 100 by pulses from the variable divider 102. However, should the rate established by variable divider 102 be greater than a predetermined minimum infusion rate, comparison circuit 114 provides an enabling signal to NAND gate 115 which allows the output signal from register 107 to enable NOR gate 117 through inverter 120. This establishes a "keep open" mode of operation wherein pulses from fixed divider 116 provide motor drive circuits 101 with stepping command signals at a frequency which maintains a desired minimum flow rate through the system.

Registers 106, 107 and 110 are automatically reset upon initial operation of the system by the auto reset circuit 130. Register 105 may also be manually reset by switch 33 when the start-stop flip-flop 121 is conditioned to a stop state.

Protection against occlusion in the administration set is provided by switch 132, which conditions flip-flop 121 to a stop state and inhibits NOR gates 154-157. Similarly, protection against the formation of bubbles within the administration set is provided by bubble detector 62, which also conditions flip-flop 121 to a stop state and inhibits NOR gates 154-157. Protection against AC line failure is provided by voltage comparator 140 which actuates relay 141 to switch stepper motor 100 to battery 138, and by voltage comparator 133 which interrupts operation of the apparatus upon occurrence of a low voltage condition for a predetermined period of time.

Upon occurrence of any one of the above alarm functions, or upon infusion of the desired fluid volume, an aural alarm 159 is actuated to alert the operator that attention to the apparatus is required. A switch associated with the pressure plate of the pump head locks out the alarm when the pump head is opened.

To avoid the need for changing the gearing between stepper motor 100 and rotor assembly 40 to eliminate the rate error, metering apparatus 10 includes, in accordance with the invention, rate compensation circuit 160. As shown in FIG. 4, compensation circuit 160 is included between variable rate multiplier 102, which generates control pulses at a user-selected rate, and motor drive circuits 101, which utilize the control pulse to generate multi-phase drive signals for stepper motor 100. Thus situated, the effect of rate compensation circuit 160 is to divide the control pulses generated by multiplier 102 by a factor which will compensate for the metering error in the metering head. This factor is preferably determined at the time of manufacture of the apparatus, and set by switches within the apparatus not normally accessible to the operator.

As shown in FIG. 5, the compensation circuit 160 is positioned at the output of OR gate 118, so as to be effective in either operating or keep open modes, while not interfering with the operation of the various protection circuits of the apparatus. Furthermore, the compensation circuit does not effect the pulses applied to divider 122 and register 105, since the metering error is not present in these devices. However, it is necessary that the division factor of divider 122 be changed to take into account the pulse rate division N introduced by compensation circuit 160 in the absence of error. Thus, if 2,353 pulses are required to be input to motor drive circuits 101 for a 1 ml. fluid transfer, then divider 122 must divide the pulses from OR gate 118 by a factor of $2,353 \times N$ to provide a ml-indicative signal to register 105.

Figure 6:
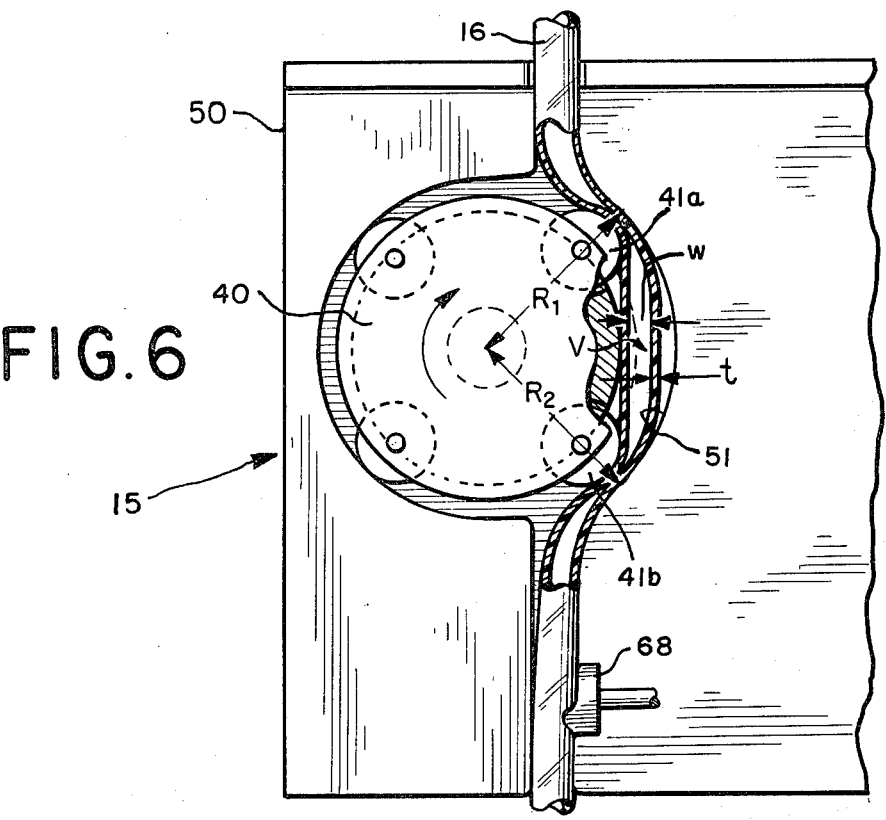
FIG. 6 is a front elevational diagrammatic view of the peristaltic metering head and platen utilized in the fluid metering apparatus of the invention.

Referring to FIG. 6, as previously developed it is possible that dimensional variations in the metering head 15 of the metering apparatus may introduce an undesirable discrepancy between the preset metering rate and the actual flow rate. This discrepancy in flow rates results because of variation in the volume V of the fluid metered between rollers 41a and 41b. Since, it is this volume V which is repeatedly urged through tubing 16 as rotor 40 turns, any variation in volume V results in a variation in flow rate.

A principal factor affecting the volume V of metered fluid is the radius R of platen surface 51. Any variation in radius R, or in radius $R_1$ at one roller and radius $R_2$ at the other roller, such as might result from different production runs of the platen at different times and locations, results in a change in metered volume V, and consequently an error in metered rate.

Another factor affecting metered volume V is the thickness T of the tubing wall, since this affects the width W of the metering chamber. Normally, the wall thickness of the 0.102 ±0.003 in I.D. vinyl tubing used in administration sets is closely controlled, being maintained at a nominal thickness of 0.019 in. and varying at maximum from +0.002 in. to −0.001 in. However, where a particular type of tubing having an abnormal wall thickness is regularly utilized, or where tubing having a wall thickness variation at one extreme is utilized in metering apparatus having a platen surface 51 near its tolerance limit, it may be desirable to provide rate compensation in the metering apparatus.

Figure 7:
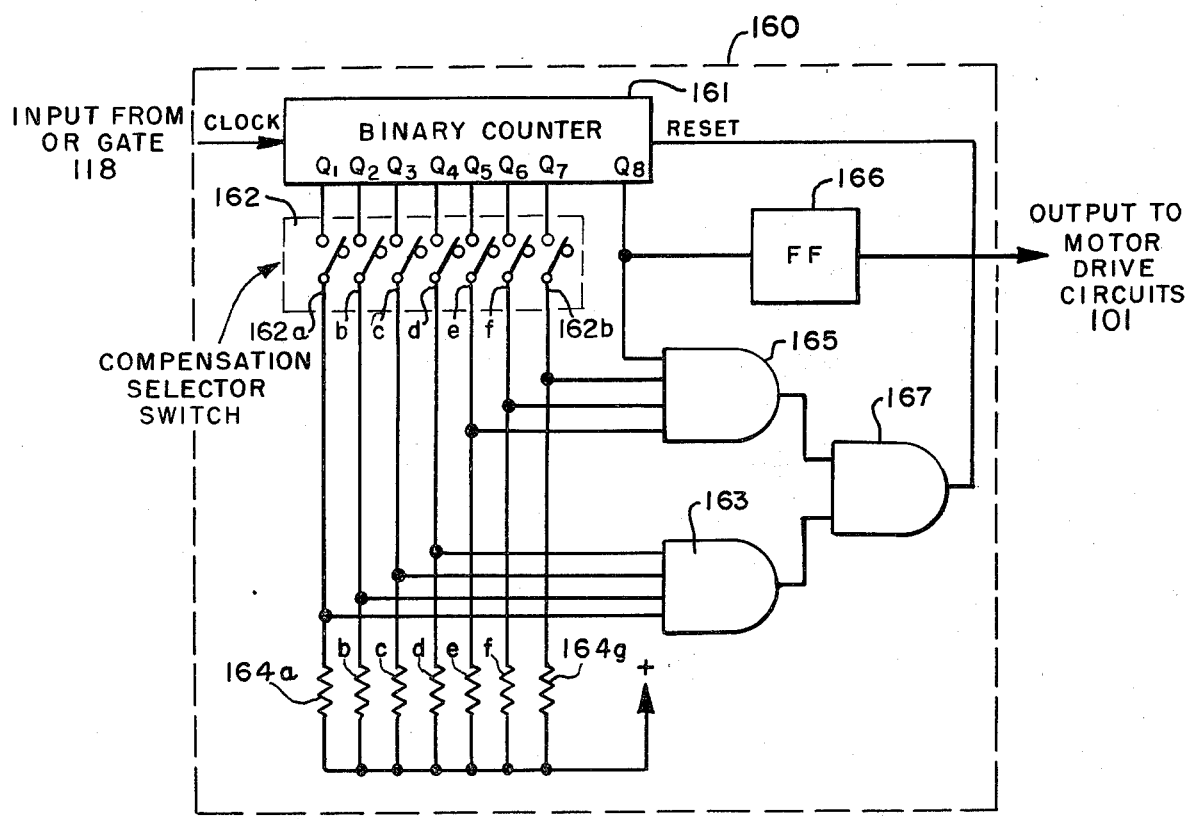
FIG. 7 is a simplified schematic diagram of the rate compensation circuit utilized in the fluid metering apparatus of the invention.

Referring to FIG. 7, rate compensation circuit 160 may be conveniently implemented by means of a conventional 12 bit binary counter 161, such as the type MC14040B manufactured by Motorola, Inc., of Schaumburg, Ill. The first four ($Q_1$–$Q_4$) of the twelve stage outputs ($Q_1$–$Q_{12}$) of this device are connected through respective ones of switches 162a–162d to respective inputs of a first four-input AND gate 163, and by respective ones of resistors 163a–163d to a source of unidirectional current. Similarly, the next three stage outputs ($Q_5$–$Q_7$) are connected through respective ones of switches 162e–162g to respective inputs of a second four-input AND gate 165. The remaining input of AND gate 165 is connected to the $Q_8$ stage output of counter 161, and to the input of a flip-flop 166. The outputs of AND gates 163 and 165 are connected to respective inputs of two-input third AND gate 167. The output of AND gate 167 is connected to the reset input of binary counter 161.

In operation, control pulses at a user-preset rate are applied to the clock input of counter 161. These pulses cause the counter to advance in a conventional manner, with the outputs of the stages of the counter becoming alternately binary one or binary zero with the advancing count. To achieve a desired compensating pulse division factor, selected ones of the counter stage outputs are connected by closure of appropriate ones of switches 162a–162g to AND gates 163 and 165. When all of the outputs thus connected are at a binary one state, AND gates 163 and 165 each produce a binary one output which is applied to a respective input of AND gate 167. This gate in turn produces a binary one output which, when applied to counter 161, causes that device to reset to an all binary zero state. The transition of the $Q_8$ output from a binary one to a binary zero state at reset causes actuation of flip-flop, 166, which functions in a conventional manner to produce a buffered output pulse for application to the motor drive circuits 101.

The actual compensation or division factor obtained from counter 161 depends on the particular ones of switches 162a–162g which are closed. Those inputs of AND gates 163 and 165 which are not connected to a counter output are biased to a binary one by associated ones of resistors 164a–164g so as to not inhibit the gates. Those inputs connected to counter outputs are held at binary zero until the associated output stage is actuated.

Because of the binary nature of the counter, the eight utilized counter stages can be considered as having the following numerical values:

| | |
|---|---|
| $Q_1$ | 1 |
| $Q_2$ | 2 |
| $Q_3$ | 4 |
| $Q_4$ | 8 |
| $Q_5$ | 16 |
| $Q_6$ | 32 |
| $Q_7$ | 64 |
| $Q_8$ | 128 |

The particular division factor of the counter can be determined by adding up the numerical values of the switch-connected counters. Thus, for example, if switches $Q_1$, $Q_4$ and $Q_5$ are closed in the illustrated embodiment (with $Q_8$ permanently connected), a division factor of $1+8+16+128=153$ is obtained.

Assuming, by way of further example, that the division factor of 153 is designated as the nominal no-error division factor N of compensating circuit 160, then positive and negative corrections can be established by setting switches 162a–162g to obtain lower and higher factors, respectively. For example, the following corrections, among others, are available:

| % Deviation of Flow Volume | Division Factor | Counter Stages Connected | | | | | | | |
|---|---|---|---|---|---|---|---|---|---|
| | | Q1 | Q2 | Q3 | Q4 | Q5 | Q6 | Q7 | Q8 |
| −8.57% | 167 | X | X | X | | | X | | X |
| −7.14% | 165 | X | | X | | | X | | X |
| −5.71% | 162 | | X | | | | X | | X |
| −4.29% | 160 | | | | | | X | | X |
| −2.86% | 157 | X | | X | X | X | | | X |
| −1.43% | 155 | X | X | | X | X | | | X |
| 0% | 153 | X | | | X | X | | | X |
| +1.43% | 151 | X | X | X | | X | | | X |
| +2.86% | 149 | X | | X | | X | | | X |
| +4.29% | 147 | X | X | | | X | | | X |
| +5.71% | 145 | X | | | | X | | | X |
| +7.14% | 143 | X | X | X | X | | | | X |
| +8.57% | 141 | X | | X | X | | | | X |
| +10.00% | 139 | X | X | | X | | | | X |
| +11.43% | 137 | X | | | X | | | | X |
| +12.86% | 135 | X | X | X | | | | | X |

Assuming the nominal "no error" division factor N=153, and a metering head requiring the application of 2,353 pulses to motor drive circuits 101 to meter the flow of 1 milliliter of fluid, it follows that $2,353 \times 153 = 360,009$, or $3.6 \times 10^5$, pulses must be produced by the variable pulse multiplier stage 102 in order to infuse 1 milliliter. Assuming a clock frequency of 200 KHZ, then $$\frac{200 \times 10^3}{\text{sec}} \times \frac{3600 \text{ sec}}{\text{hour}} \times K = 3.6 \times 10^5, \text{ or } K = .0005,$$

where K is the necessary multiplication factor of multiplier stage 102 for a 1 ml/hour rate. This rate is set by the operator by setting register 110 in the manner previously described.

In order for register 105 to accurately record volume infused in units of one milliliter, it is necessary that divider circuit apply the same $3.6 \times 10^5$ nominal conversion factor applied at the input of compensation circuit 160. If other units are to be recorded, then a different correction factor appropriate to the displayed units would be required.

Flip-flop 166 is a conventional Schmitt trigger and is provided to generate an output pulse of predetermined amplitude and duration following each reset of counter 161. However, in appropriate circumstances other types of flip-flops, such as JK flip-flops, may be used instead and connected to provide an output only on alternate resets, thereby introducing an additional division factor of two.

In a preferred construction, switches 162a–162g may be contained within a single 7 switch circuit board-mounted DIP assembly within the metering apparatus housing. Then at some point in the manufacturing process, following a calibration test, the switches can be set by a technician as required to compensate for observed errors in flow rate.

While the compensation circuit has been shown in conjunction with a rotary-type peristaltic pump, it will be appreciated that the circuit is also useful in conjunction with linear-type stepper motor-driven peristaltic pumps, wherein metering inaccuracies may arise with variations in tubing dimensions. Furthermore, it will be appreciated that in either rotary or linear-type pumps the compensation switches 162 may be located either within the metering apparatus housing, for factory adjustment, or at a location accessible from the exterior of the housing for setting by an operator, as when compensating for particular types of tubing.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

We claim:

1. Metering apparatus for establishing a desired fluid flow rate through a fluid administration set of the type including a compressible tubing segment, said apparatus comprising, in combination:
   a housing;
   a flow metering head including a rotor mounted on said housing for rotation about a fixed axis, said rotor including a plurality of pressure rollers disposed about the circumference thereof, and a pressure plate for positioning the compressible tubing segment in compressive engagement with at least a portion of said rollers, whereby an incremental volume of fluid is pumped through said tubing segment with a predetermined increment of rotation of said rotor, said incremental volume of fluid being subject to variation from dimensional variations in the flow metering head;
   means including a stepper motor for driving said rotor;
   a source of repetitive clock pulses;
   rate setting means comprising a first frequency divider responsive to said repetitive clock pulses for providing a first output signal, the division factor of said first divider being user-presettable according to the desired fluid flow rate;
   rate compensation means comprising a second frequency divider responsive to said first output signal for providing a second output signal; and
   motor drive circuit means responsive to said second output signal for applying motor control signals to said stepper motor according to the frequency of said second output signal, said second frequency divider providing a preset division factor compensating said first output signal for the variation in said incremental volume brought about by dimensional variations in said metering head whereby the desired flow rate is established in the administration set.

2. Fluid metering apparatus as defined in claim 1 wherein said first and second signals comprise pulse signals, and said stepper motor advances said rotor one increment of rotation upon occurrence of a predetermined number of said second pulse signals.

3. Fluid metering apparatus as defined in claim 2 wherein said second frequency divider comprises a binary counter, said first output pulses being applied to the clock input of said counter, and wherein at least one logic gate having inputs coupled to the outputs of said counter is provided for resetting said counter upon said counter obtaining a preset count.

4. Fluid metering apparatus as defined in claim 2 including a plurality of switches for selectively connecting said outputs of said counter to said inputs of said logic gate.

5. Fluid metering apparatus as defined in claim 4 wherein said plurality of switches are contained within the housing of the metering apparatus and are not readily accessible to the operator of the apparatus.

6. In a metering apparatus for establishing a desired fluid flow rate through a fluid administration set of the type including a compressible tubing segment, and wherein the metering apparatus is of the type comprising,
   a housing,
   a flow metering head assembly including rotor mounted on said housing for rotation about a fixed axis, the rotor including a plurality of pressure rollers disposed about the circumference thereof and a pressure plate for positioning the compressible tubing segment in compressive engagement with at least a portion of the rollers, whereby an incremental volume of fluid is pumped through the tubing segment with a predetermined increment of rotation of the rotor, the incremental volume of fluid being subject to variation from dimensional variations in the flow metering head,
   a stepper motor for driving the rotor,
   rate setting means comprising a first frequency divide providing a first output signal, the division factor of the first divider being user-adjustable according to the desired flow rate, and
   motor drive means responsive to an applied control signal for incrementally advancing the stepper motor,
   the improvement comprising:
   rate compensation means comprising a second frequency divider responsive to the first output signal for providing a control signal to said motor drive means, said frequency divider providing a preset division factor compensating the first output signal for the variation in the incremental volume brought about by dimensional variations in the metering head whereby the desired flow is established in the administration set.

7. Fluid metering apparatus as defined in claim 6 wherein said first and second signals comprise pulse signals, and said stepper motor advances said rotor one increment of rotation upon occurrence of a predetermined number of said second pulse signals.

8. Fluid metering apparatus as defined in claim 7 wherein said frequency divider comprises a binary counter, said first output pulses being applied to the clock input of said counter, and wherein at least one logic gate having inputs coupled to the outputs of said counter is provided for resetting said counter upon said counter obtaining a preset count.

9. Fluid metering apparatus as defined in claim 6 including a plurality of switches for selectively connecting said outputs of said counter to said inputs of said logic gate.

10. Fluid metering apparatus as defined in claim 9 wherein said plurality of switches are contained within the housing of the metering apparatus and are not readily accessible to the operator of the apparatus.

11. Metering apparatus for establishing a desired fluid flow rate through a fluid infusion set of the type including a compressible tubing segment, said apparatus comprising, in combination:

a housing;

a flow metering head including a rotor mounted on said housing for rotation about a fixed axis, said rotor including a plurality of pressure rollers disposed about the circumference thereof, and a pressure plate for positioning the compressible tubing segment in compressive engagement with at least a portion of said rollers, whereby an incremental volume of fluid is pumped through said tubing segment with a predetermined increment of rotation of said rotor, said incremental volume of fluid being subject to variation from dimensional variations in the flow metering head;

means including a stepper motor for driving said rotor;

a source of repetitive clock pulses;

rate setting means comprising a first counter responsive to said repetitive clock pulses for providing a first output pulse upon the occurrence of a predetermined number of clock pulses, the division factor of said first counter being user-presettable according to the desired fluid flow rate;

rate compensation means comprising a second counter responsive to said first output pulses for providing a second output pulse upon the occurrence of a predetermined number of said first output pulses; and motor drive circuit means responsive to said second output pulses for applying motor control signals to said stepper motor according to the occurrence of said second output pulses, said second counter providing a preset division factor compensating said first output pulses for the variation in said incremental volume brought about by dimensional variations in said metering head whereby the desired flow rate is established in the administration set.

12. Fluid metering apparatus as defined in claim 11 wherein said second pulse divider comprises a binary counter, said first output pulses being applied to the clock input of said counter, and at least one logic gate having inputs coupled to the outputs of said counter for resetting said counter upon said counter obtaining a preset count.

13. Fluid metering apparatus as defined in claim 12 including a plurality of switches for selectively connecting said outputs of said counter to said inputs of said logic gate.

14. Fluid metering apparatus as defined in claim 13 wherein said plurality of switches are contained within the housing of the metering apparatus and are not readily accessible to the operator of the apparatus.

* * * * *